United States Patent [19]

Garner

[11] 4,180,656

[45] Dec. 25, 1979

[54] AZOMETHINE COMPOUNDS

[75] Inventor: Robert Garner, Bury, England

[73] Assignee: Ciba-Geigy Corporation, Ardsley, N.Y.

[21] Appl. No.: 787,806

[22] Filed: Apr. 15, 1977

[30] Foreign Application Priority Data

Apr. 27, 1976 [GB] United Kingdom ............ 17023/76

[51] Int. Cl.² ........................................... C07C 119/00
[52] U.S. Cl. .............................. 542/423; 260/556 B; 106/288 Q
[58] Field of Search .................... 260/556 AR, 556 B; 106/288 Q; 542/423

[56] References Cited

U.S. PATENT DOCUMENTS

| | | | |
|---|---|---|---|
| 2,730,457 | 1/1956 | Green et al. | 428/307 |
| 2,800,457 | 7/1957 | Green et al. | 252/316 |
| 2,932,582 | 4/1960 | Pesa et al. | 428/307 |
| 3,051,702 | 8/1962 | Fitchett et al. | 260/556 AR |
| 3,418,250 | 12/1968 | Vassiliades | 424/17 |
| 3,418,656 | 12/1968 | Vassiliades | 424/17 |
| 3,427,180 | 2/1969 | Phillips, Jr. | 428/306 |
| 3,516,846 | 6/1970 | Matson | 424/32 |
| 3,923,793 | 12/1975 | Mundlos et al. | 260/556 B |
| 4,042,582 | 8/1977 | Papenfuhs | 106/288 Q |

FOREIGN PATENT DOCUMENTS

| | | |
|---|---|---|
| 989264 | 3/1962 | United Kingdom . |
| 1042596 | 9/1966 | United Kingdom . |
| 1042597 | 9/1966 | United Kingdom . |
| 1042598 | 9/1966 | United Kingdom . |
| 1042599 | 9/1966 | United Kingdom . |
| 1053935 | 1/1967 | United Kingdom . |
| 1156725 | 7/1969 | United Kingdom . |

*Primary Examiner*—Winston A. Douglas
*Assistant Examiner*—J. V. Howard
*Attorney, Agent, or Firm*—Prabodh I. Alumaula

[57] ABSTRACT

An azomethine compound of the general formula

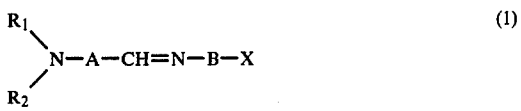

(1)

wherein
A and B, independently of the other, represent naphthylene or phenylene which are unsubstituted or substituted by halogen, cyano, nitro, lower alkyl, lower alkoxy, benzyloxy or phenoxy,
X represents a group of the formula

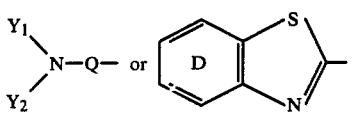

(1a)        (1b)

$R_1$ and $Y_1$ each represents alkyl of at most 12 carbon atoms which is unsubstituted or substituted by halogen, hydroxyl, cyano, lower alkoxy or lower alkyl-carbonyloxy; cycloalkyl, phenyl, benzyl or phenyl or benzyl which are substituted by halogen, nitro, lower alkyl or lower alkoxy,
$R_2$ and $Y_2$ each represents hydrogen, alkyl of at most 12 carbon atoms which is unsubstituted or substituted by halogen, hydroxyl, cyano, lower alkoxy or lower alkyl-carbonyloxy; cycloalkyl, benzyl or benzyl which is substituted by halogen, nitro, lower alkyl or lower alkoxy or each pair of substituents
$R_1$ and $R_2$ or $Y_1$ and $Y_2$, together with the nitrogen atom to which they are attached, independently represents a 5- or 6-membered heterocyclic radical,
Q represents —CO— or —SO₂— and the benzene ring D is unsubstituted or substituted by halogen, nitro, lower alkyl or lower alkoxy; these compounds are particularly useful as color formers which give intense yellow or orange shades of excellent light fastness when they are brought into contact with an electron-accepting coreactant.

4 Claims, No Drawings

AZOMETHINE COMPOUNDS

The present invention provides novel azomethine compounds, a process for their manufacture and their use as colour formers in pressure-sensitive or thermoreactive recording systems.

The azomethine compounds of the present invention have the general formula

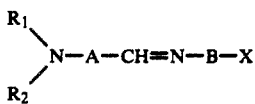 (1)

wherein
A and B, independently of the other, represent naphthylene or phenylene which are unsubstituted or substituted by halogen, cyano, nitro, lower alkyl, lower alkoxy, benzyloxy or phenoxy,
X represents a group of the formula

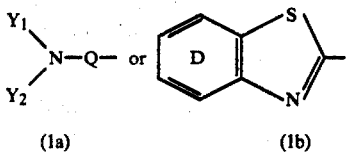

(1a)        (1b)

$R_1$ and $Y_1$ each represents alkyl of at most 12 carbon atoms which is unsubstituted or substituted by halogen, hydroxyl, cyano, lower alkoxy or lower alkyl-carbonyloxy; cycloalkyl, phenyl, benzyl or phenyl or benzyl which are substituted by halogen, nitro, lower alkyl or lower alkoxy,
$R_2$ and $Y_2$ each represents hydrogen, alkyl of at most 12 carbon atoms which is unsubstituted or substituted by halogen, hydroxyl, cyano, lower alkoxy or lower alkyl-carbonyloxy; cycloalkyl, benzyl or benzyl which is substituted by halogen, nitro, lower alkyl or lower alkoxy or each pair of substituents
$R_1$ and $R_2$ or $Y_1$ and $Y_2$, together with the nitrogen atom to which they are attached, independently represents a 5- or 6- membered, preferably saturated, heterocyclic radical,
Q represents —CO— or preferably —SO$_2$— and the benzene ring D is unsubstituted or substituted by halogen, nitro, lower alkyl or lower alkoxy.

In the definition of the radicals of the azomethine compounds lower alkyl and lower alkoxy groups are normally to be understood as meaning those groups or group components that contain 1 to 5, in particular 1 to 3, carbon atoms, for example methyl, ethyl, n-propyl, isopropyl, n-butyl, sec. butyl or amyl, methoxy or ethoxy. When benzyl is substituted, it is understood that it is, as a rule, substituted on the aromatic nucleus thereof.

If the substituents $R_1$, $R_2$, $Y_1$ and $Y_2$ represent alkyl groups, they can be branched-chain or, preferably, straight-chain alkyl radicals. Examples of such alkyl radicals are methyl, ethyl, n-propyl, isopropyl, n-butyl, sec.-butyl, n-hexyl, n-octyl or n-dodecyl.

If the alkyl radicals in the definition of $R_1$, $R_2$, $Y_1$ and $Y_2$ are substituted, the radicals are, above all, halogenalkyl, hydroxyalkyl, cyanoalkyl and alkoxyalkyl with 2 to 4 carbon atoms in each case, such as, for example, β-chloroethyl, β-hydroxyethyl, β-cyanoethyl, β-methoxyethyl or β-ethoxyethyl. If the alkyl groups in $R_1$, $R_2$, $Y_1$ and $Y_2$ contain a lower alkyl-carbonyloxy group, then this latter group is for example an acetyloxy or propionyloxy group.

Examples for cycloalkyl in the definition of $R_1$, $R_2$, $Y_1$ and $Y_2$ include cyclopentyl or preferably cyclohexyl.

Preferred substituents which may be present in the benzyl groups of the R and Y substituents and in the phenyl group of $R_1$ and $Y_1$ are halogens, nitro, methyl and methoxy. Examples of these araliphatic and aromatic radicals are: o- or p-methyl benzyl, o- or p-chlorobenzyl, o- or p-nitrobenzyl, o- or p-tolyl, xylyl, o-, m- or p-chlorophenyl, o- or p-nitrophenyl, o- or p-methoxyphenyl.

An heterocyclic radical represented by the pairs of substituents $R_1$ and $R_2$ and $Y_1$ and $Y_2$, together with the corresponding nitrogen atom to which they are attached, is for example pyrrolidino, piperidino, pipecolino, morpholino, thiomorpholino or piperazino.

The divalent radicals A and B are preferably phenylene which can be unsubstituted or substituted by halogen, lower alkyl such as methyl or by lower alkoxy such as methoxy. The substituents $R_1$ and $R_2$ are preferably benzyl or lower alkyl. The substituent X is preferably the group of formula (1a) wherein Q represents the —SO$_2$— bridge. However, the group of formula (1b) is also an important substituent of the phenylene radical B. The radical $Y_3$ is especially lower alkyl, phenyl or phenyl which is substituted by halogen, lower alkyl or lower alkoxy. $Y_4$ is preferably hydrogen or lower alkyl such as methyl or ethyl.

The benzene ring D is preferably not further substituted or contains primarily halogen, lower alkyl, preferably methyl, or lower alkoxy such as methoxy.

Halogens in the above mentioned substituents as well as in the substituents which follow are, for example, fluorine, bromine or, preferably, chlorine.

Preeminent compounds of the general formula (1) have the following general formula

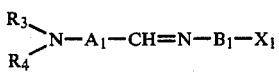 (2)

wherein
$A_1$ and $B_1$, independently of the other, represent phenylene which is unsubstituted or substituted by halogen, lower alkyl or lower alkoxy,
$X_1$ represents a group of the formula

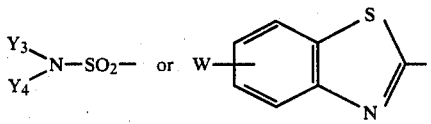

(2a)        (2b)

$R_3$ and $R_4$ independently of the other, represent lower alkyl, benzyl or benzyl which is substituted by halogen, nitro, lower alkyl or lower alkoxy,
$Y_3$ represents lower alkyl, phenyl or phenyl which is substituted by halogen, lower alkyl or lower alkoxy,
$Y_4$ represents hydrogen or lower alkyl or each pair of substituents
$R_3$ and $R_4$ or $Y_3$ and $Y_4$, together with the nitrogen atom to which they are attached, independently represents pyrrolidino, piperidino or morpholino and W represents hydrogen, halogen, lower alkyl or lower alkoxy.

Of special interest are azomethine compounds falling under formulae (1) and (2) and having the formula

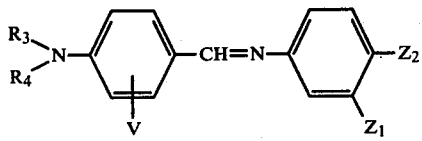 (3)

wherein
of $Z_1$ and $Z_2$ one represents a group of the formula (2a) or (2b) and the other represents hydrogen, halogen, lower alkyl such as methyl or lower alkoxy such as methoxy, V represents hydrogen, halogen, methyl or methoxy and $R_3$ and $R_4$ have the given meanings.

Particularly valuable azomethine compounds of the above formulae (1), (2) and (3), which can be employed in the colour reactant system of a recording material, are those listed hereinafter under (A) and (B):

(A) azomethine compounds of the general formula

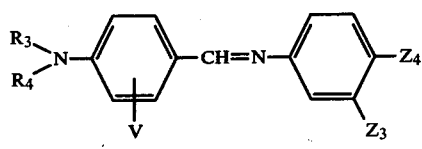 (4)

wherein
of $Z_3$ and $Z_4$ one represents a group of the formula (2a) and the other represents hydrogen, halogen, lower alkyl such as methyl or lower alkoxy such as methoxy and $R_3$, $R_4$ and V have the given meanings.

Amongst these azomethine compounds of formula (4), those in which $R_3$ and $R_4$ both represent methyl, ethyl or benzyl, V represents hydrogen or chlorine, $Z_3$ represents the group of the formula

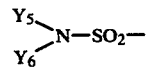 (3a)

$Y_5$ represents methyl, ethyl or phenyl,
$Y_6$ represents hydrogen, methyl or ethyl
or $Y_5$ and $Y_6$, together with the nitrogen atom to which they are attached, represent pyrrolidino or piperidino and $Z_4$ represents hydrogen or methyl, are preferred.

(B) azomethine compounds of the general formula

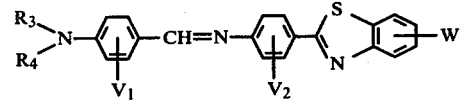 (5)

wherein
$V_1$ and $V_2$, independently of the other, represent hydrogen, halogen, methyl or methoxy and
$R_3$, $R_4$ and W have the given meanings.

Amongst these compounds of formula (5), those in which $R_3$ and $R_4$ represent methyl, ethyl or benzyl, $V_1$ and $V_2$ represent hydrogen and W represents methyl, are preferred.

The azomethine compounds of formulae (1) to (5) are obtained by processes which are known per se. One process for the manufacture of the azomethine compounds of formula (1) comprises reacting an aldehyde compound of the general formula

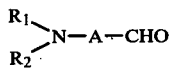 (6)

with an amino compound of the general formula

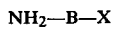 (7)

$NH_2$—B—X wherein A, B, $R_1$, $R_2$ and X have the given meanings.

The reaction is advantageously carried out in an organic solvent and optionally in the presence of a catalyst, e.g. acetic acid or a tertiary amine. Such solvent may be any organic solvent which is unreactive towards the reactants or products and is preferably a lower aliphatic alcohol such as methanol, ethanol or isopropanol.

As a rule substantially equimolar amounts of the reactants are condensed, advantageously at 40° to 80° C.

The azomethine compounds of formulae (1) to (5) are normally colourless or only weakly coloured. When these colour formers are brought into contact with a developer, i.e. an electron acceptor, they produce yellow or orange colours of deep intensity, absorbing light in the range of 400 to 520 nm with maxima usually within the range of 440 to 470 nm. The obtained colours are of excellent light fastness. Moreover, the new azomethine compounds are inert as regards premature reactivity, fogging and sublimation. They are very useful when mixed with other known colour formers such as phthalides, fluorans, spiropyrans, triarylmethane leuco dyes, substituted phenoxazines or phenothiazines, in order to produce blue, navy blue, grey or black colours.

Examples of suitable known colour formers for the mixtures with the novel azomethines are Crystal violet lactone, 3,3-(bis-amino-phenyl)-phthalides, 3,3-(bis-subst. indolyl)-phthalides, 3-(aminophenyl)-3-indolyl-phthalides, 6-diethylamino-2-n-octylamino-fluoran, bis-(aminophenyl)-furyl or -phenyl methanes or benzoyl leucomethylene blue.

The colour formers of formulae (1) to (5) are especially suitable for use in a pressure-sensitive or heat-sensitive recording material.

A pressure-sensitive material comprises for example at least a pair of sheets which contain at least one colour former of formulae (1) to (5), dissolved in an organic solvent and a solid electron acceptor as developer.

Typical examples of such electron acceptors are attapulgite clay, silton clay, silica, bentonite, halloysite, aluminium oxide, aluminium sulphate, aluminium phosphate, zinc chloride, kaolin or any acid clay or acid reacting organic compounds such as optionally ring substituted phenols, salicylic acid or esters or metal salts of this latter, further any acid polymeric material, for example a phenolic polymer, an alkylphenolacetylene resin, a maleic acid/rosin resin or a partially or completely hydrolysed polymer of maleic acid and styrene, ethylene vinyl methyl ether or carboxy-polymethylene.

Preferred developers are attapulgite clay, silton clay or phenolformaldehyde resins. These electron acceptors are preferably applied in the form of a layer to the face of the receiver sheet.

The colour former effects a coloured marking at those points at which it comes into contact with the electron acceptor.

The colour formers which are present in the pressure-sensitive recording material are preferably separated from the electron acceptor in order to prevent them from becoming active too soon. This can be accomplished as a rule by incorporating the colour formers in foam-like, sponge-like or honeycomb-like structures. Preferably, the colour formers are enclosed in microcapsules which can be ruptured by pressure.

When the capsules are burst by pressure, for example with a pencil and the colour former solution is thus transferred to an adjacent sheet which is coated with an electron acceptor, a coloured image is produced. This new colour results from the dye which is thereby formed and which absorbs in the visible range of the electromagnetic spectrum.

The colour formers may be encapsulated preferably in the form of solution in organic solvents. Examples of suitable solvents are preferably non-volatile solvents, for example polyhalogenated diphenyl, such as trichlorodiphenyl or a mixture thereof with liquid paraffin, tricresyl phosphate, di-n-butyl phthalate, dioctyl phthalate, trichlorobenzene, nitrobenzene, trichloroethyl phosphate, petroleum ether, hydrocarbon oils, such as paraffin, alkylated derivatives of naphthalene or diphenyl, terphenyls, partially hydrogenated terphenyl or other chlorinated or hydrogenated condensed aromatic hydrocarbons. The capsule walls can be formed evenly around the droplets of the colour former solution by coacervation, in which case the encapsulating material can consist of gelatin and gum arabic, as described e.g. in U.S. Pat. No. 2,800,457.

The capsules can also be formed from an aminoplast or from modified aminoplasts by polycondensation as described in the British patent specifications Nos. 989,264 and 1,156,725.

The microcapsules containing the colour formers of formula (1) can be used for the manufacture of pressure-sensitive copying materials of the most widely different known kinds. The various systems differ substantially from one another in the arrangement of the capsules, the colour reactants and the carrier material.

A preferred arrangement consists in applying the encapsulated colour formers as a layer to the back of a transfer sheet and the electron acceptor substance as a layer to the face of a receiving sheet. However, the components can also be used in the paper pulp.

Another arrangement of the constituents consists in the microcapsules which contain the colour former and the colour reactants, being in or on the same sheet in the form of one or more individual sheets or being present in the paper pulp.

Such pressure-sensitive copying materials are described, for example, in U.S. Pat. Nos. 2,730,457, 2,932,582, 3,418,250, 3,418,656, 3,427,180 and 3,516,846. Further systems are described in British patent specifications Nos. 1,042,596, 1,042,597, 1,042,598, 1,042,599, and 1,053,935. Microcapsules which contain the colour formers of formula (1) are suitable for each of these systems and for other pressure-sensitive systems.

The capsules are preferably secured to the carrier by means of a suitable adhesive. Since paper is the preferred carrier material, these adhesives are principally paper coating agents, for example gum arabic, polyvinyl alcohol, hydroxymethyl cellulose, casein, methyl cellulose or dextrin.

The term "paper" used herein comprises not only normal paper made from cellulose fibres, but also paper in which the cellulose fibres are replaced (partially or completely) by synthetic polymer fibres.

The colour formers of formulae (1) to (5) can also be used in a thermoreactive recording material. This recording material consists normally at least of a carrier, a colour former, an electron acceptor and optionally a binder. Thermoreactive recording systems comprise, for example, heat-sensitive recording and copying materials and papers. These systems are used, for example, for recording information, e.g. in electronic computers, teleprinters or telewriters and in measuring instruments. The image (mark) formation can also be affected manually with a heated pen. Laser beams can also be used to produce heat-induced marks. The thermoreactive recording material can be so composed that the colour former is dispersed or dissolved in one binder layer and the developer is dissolved or dispersed in the binder in a second layer. A second possibility consists in dispersing both the colour former and the developer in the binder in one layer. By means of heat the binder is softened at specific areas and the colour former comes into contact with the electron acceptor substance at those points at which heat is applied and the desired colour develops at once.

The developers are the same electron-accepting substances as are used in pressure-sensitive papers. For practical purposes the developer should be solid at room temperature and melt or soften above 50° C. Examples of developers in heat-sensitive systems are the clays or phenolic resins already mentioned or phenolic compounds, for example 4-tert. butylphenol, 4-phenylphenol, 4-hydroxydiphenyl oxide, α-naphthol, β-naphthol, 4-hydroxybenzoic acid methyl ester, 4-hydroxyacetophenone, 2,2'-dihydroxydiphenyl, 4,4-isopropylidene-diphenol, 4,4'-isopropylidene-bis-(2-methylphenol), 4,4'-bis-(hydroxyphenyl)valeric acid, hydroquinone, pyrogallol, chloroglucinol, p-, m- and o-hydroxybenzoic acid, gallic acid, 1-hydroxy-2-naphthoic acid, as well as boric acid and aliphatic dicarboxylic acids, e.g. tartaric acid, oxalic acid, maleic acid, citric acid, citraconic acid or succinic acid.

Fusible, film-forming binders are preferably used for the manufacture of the thermoreactive recording material. These binders are normally water-soluble, whereas the colour formers and the developer are insoluble in water. The binder should be able to disperse and fix the colour former and the developer at room temperature.

By applying heat the binder softens or melts, so that the colour former comes in contact with the developer and a colour is able to form. Examples of binders which are soluble or at least swellable in water are hydrophilic polymers, for example polyvinyl alcohol, polyacrylic acid, hydroxyethyl cellulose, methyl cellulose, carboxymethyl cellulose, polyacrylic amide, polyvinyl pyrrolidone, gelatin and starch.

If the colour former and the developer are in two separate layers, it is possible to use water-insoluble binders, i.e. binders which are soluble in non-polar or only weakly polar solvents, for example natural rubber, synthetic rubber, chlorinated rubber, alkyd resins, polystyrene, styrene/butadiene copolymers, polymethylmethacrylates, ethyl cellulose, nitrocellulose and polyvinyl carbazole. The preferred arrangement, however, is that in which the colour former and the developer are contained in one layer in a water-soluble binder.

The thermoreactive coatings can contain further additives. The coatings can contain, for example, talc, TiO₂, ZnO or CaCO₃ or also organic pigments, for example urea/formaldehyde polymers for improving the degree of whiteness, facilitating the printing of papers and for preventing the heated pen from sticking. In order to effect the colour formation only within a limited temperature range, it is possible to add substances such as urea, thiourea, acetanilide, phthalic anhydride or other appropriate fusible products which induce the simultaneous melting of the colour former and developer.

The following Examples illustrate the invention, the percentages being by weight unless otherwise stated.

EXAMPLE 1

14.9 g of 4-dimethylaminobenzaldehyde, 24.0 g of 2-(4'-aminophenyl)-6-methyl-benzothiazole and 150 ml of methanol are heated at the boil for three hours. The precipitate obtained on cooling the reaction solution is filtered off, washed with methanol and dried at 60° C. 34.9 g of an azomethine compound of the formula

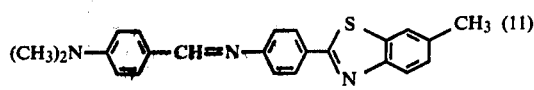

are thus obtained. This compound melts at 236°–237° C. A solution of this compound in 95% acetic acid has λ maximum at 461 nm. When contacted with silton clay coated paper, this azomethine compound develops an intense orange colour.

The above procedure is repeated, but substituting equivalent amounts of corresponding benzaldehyde compounds and amino compounds for the 4-dimethylaminobenzaldehyde and the 2-(4'-aminophenyl)-6-methyl-benzothiazole to yield the azomethine compounds of the formula

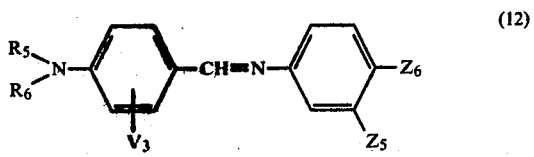

listed in the following table. The last column of the Table indicates the shades which are produced when the colour formers are brought into contact with silton clay.

Table

| Ex. No. | $R_5$ | $R_6$ | $V_3$ | $Z_5$ | $Z_6$ | melting point °C. | λmax in 95% acetic acid nm | shade on silton-clay |
|---|---|---|---|---|---|---|---|---|
| 2 | C₂H₅ | C₂H₅ | H | H | ⟨S/N benzothiazole⟩-CH₃ | 215–216 | 465 | orange |
| 3 | n-C₃H₇ | n-C₃H₇ | H | H | ⟨S/N benzothiazole⟩-CH₃ | 144–145 | 466 | orange |
| 4 | n-C₆H₁₃ | n-C₆H₁₃ | H | H | ⟨S/N benzothiazole⟩-CH₃ | 104 | 467 | orange |
| 5 | —CH₂—⟨C₆H₅⟩ | —CH₂—⟨C₆H₅⟩ | H | H | ⟨S/N benzothiazole⟩-CH₃ | 181 | 460 | orange |
| 6 | —CH₂—⟨C₆H₅⟩ | —C₂H₅ | H | H | ⟨S/N benzothiazole⟩-CH₃ | 167–168 | 460 | orange |
| 7 | CH₃ | CH₃ | H | —SO₂—N(C₂H₅)(C₆H₅) | CH₃ | 130–131 | 442 | yellow |
| 8 | CH₃ | CH₃ | H | —SO₂—NH—⟨C₆H₅⟩ | CH₃ | 138–139 | 446 | yellow |
| 9 | C₂H₅ | C₂H₅ | H | —SO₂—NH—⟨C₆H₅⟩ | CH₃ | 173–174 | 450 | yellow |
| 10 | —CH₂—⟨C₆H₅⟩ | —CH₂—⟨C₆H₅⟩ | H | —SO₂—NH—⟨C₆H₅⟩ | CH₃ | 165 | 442 | yellow |
| 11 | CH₃ | CH₃ | 2-Cl | —SO₂—NH—⟨C₆H₅⟩ | CH₃ | 174 | 451 | yellow |
| 12 | CH₃ | CH₃ | H | —SO₂—NH—CH₃ | CH₃ | 159–160 | 446 | yellow |
| 13 | CH₃ | CH₃ | H | —SO₂—N⟨piperidine⟩ | CH₃ | oil | 446 | yellow |

Table-continued

| Ex. No. | R5 | R6 | V3 | Z5 | Z6 | melting point °C. | λmax in 95% acetic acid nm | shade on silton-clay |
|---|---|---|---|---|---|---|---|---|
| 14 | $C_2H_5$ | $C_2H_5$ | 2-$OC_2H_5$ | H | 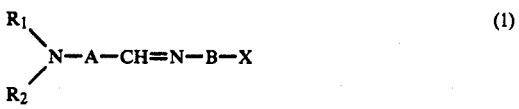 | 143–147 | 447 | yellow/orange |
| 15 | $C_2H_5$ | $C_2H_5$ | 2-$CH_3$ | H |  | 138–142 | 445 | yellow/orange |
| 16 | | $CH_2-CH_2$ $\;\;\;\;\;\;$ $CH_2\;\;CH_2$ | 2-O—$CH_3$ | H | 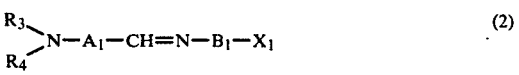 | 170–172 | 455 | yellow/orange |

EXAMPLE 17

Manufacture of a Pressure-Sensitive Copying Paper

A solution of 1 g of azomethine compound according to Example 5 in 99 g of partially hydrogenated terphenyl is emulsified in a solution of 12 g of pigskin gelatine in 88 g of water at 50° C., then a solution of 12 g gum arabic in 88 g of water at 50° C. is added. The emulsion is diluted by adding 200 g of water at 50° C. and coacervation is brought about by pouring into 600 g of ice-water and stirring for 3 hours. The resulting suspension is coated on paper and dried. When this paper is placed with its coated side adjacent to a sheet of paper coated with silton clay and writing or typing is performed upon the top sheet, a stable orange copy is made upon the coreactive sheet.

Corresponding effects are obtained by using each of the other colour formers of Examples 1 to 4 and 6 to 16.

EXAMPLE 18

A solution of 1.3 g of Crystal violet lactone, 1.3 g of bis-(4-dimethylaminophenyl)-2'-furylmethane, 0.42 g of azomethine compound according to Example 2 in 97 g partially hydrogenated terphenyl is treated as in Example 17. The resultant image on paper coated with silton clay is a dark blue of good stability.

EXAMPLE 19

A solution of 1.5 g of Crystal violet lactone, 3.0 g of bis-(4-dimethylaminophenyl)-2'-furylmethane, 0.75 g of azomethine compound according to Example 2 in 96 g partially hydrogenated terphenyl is treated as in Example 17. The resultant image on paper coated with silton clay is black of good stability.

EXAMPLE 20

A solution of 0.77 g of Crystal violet lactone, 1.54 g of bis-(4-dimethylaminophenyl)-2'-furylmethane, 0.7 g of azomethine compound according to Example 9 in 97 g partially hydrogenated terphenyl is treated as in Example 17. The resultant image on paper coated with silton clay is green of good stability.

Manufacture of a Thermoreactive Paper

EXAMPLE 21

6 g of an aqueous dispersion containing 1.57% of the azomethine compound according to Example 1 and 6.7% of polyvinyl alcohol are mixed with 134 g of an aqueous dispersion containing 14% 4,4'-isopropylidenediphenol, 8% attapulgus clay and 6% polyvinyl alcohol and is coated on paper and dried. When contacted with a heated stylus a strong orange mark is obtained which has an excellent fastness to light.

Similar results are obtained by using any other colour former obtained in Examples 2 to 16.

I claim:

1. An azomethine compound of the general formula $$\begin{matrix} R_1 \\ \phantom{R}\searrow \\ \phantom{RR}N-A-CH=N-B-X \\ \phantom{R}\nearrow \\ R_2 \end{matrix} \qquad (1)$$

wherein

A and B, independently of the other, represent naphthylene or phenylene which are unsubstituted or substituted by halogen, cyano, nitro, lower alkyl, lower alkoxy, benzyloxy or phenoxy, X represents a group of the formula $$\begin{matrix} Y_1 \\ \phantom{Y}\searrow \\ \phantom{YY}N-Q- \\ \phantom{Y}\nearrow \\ Y_2 \end{matrix} \qquad (1a)$$

$R_1$ and $Y_1$ each represents alkyl of at most 12 carbon atoms which is unsubstituted or substituted by halogen, hydroxyl, cyano, lower alkoxy or lower alkyl-carbonyloxy; cycloalkyl, phenyl, benzyl or phenyl or benzyl which are substituted by halogen, nitro, lower alkyl or lower alkoxy, $R_2$ and $Y_2$ each represents hydrogen, alkyl of at most 12 carbon atoms which is unsubstituted or substituted by halogen, hydroxyl, cyano, lower alkoxy or lower alkyl-carbonyloxy; cycloalkyl, benzyl or benzyl which is substituted by halogen, nitro, lower alkyl or lower alkoxy or each pair of substituents $R_1$ and $R_2$ or $Y_1$ and $Y_2$, together with the nitrogen atom to which they are attached, independently represents a 5- or 6- membered heterocyclic radical, and Q represents -$SO_2$.

2. An azomethine compound according to claim 1, of the general formula $$\begin{matrix} R_3 \\ \phantom{R}\searrow \\ \phantom{RR}N-A_1-CH=N-B_1-X_1 \\ \phantom{R}\nearrow \\ R_4 \end{matrix} \qquad (2)$$

wherein

A₁ and B₁, independently of the other, represent phenylene which is unsubstituted or substituted by halogen, lower alkyl or lower alkoxy, X₁ represents a group of the formula

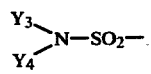  (2a)

R₃ and R₄ independently of the other, represent lower alkyl, benzyl or benzyl which is substituted by halogen, nitro, lower alkyl or lower alkoxy, Y₃ represents lower alkyl, phenyl or phenyl which is substituted by halogen, lower alkyl or lower alkoxy, Y₄ represents hydrogen or lower alkyl or each pair of substituents R₃ and R₄ or Y₃ and Y₄, together with the nitrogen atom to which they are attached, independently represents pyrrolidino, piperidino or morpholino.

3. An azomethine compound according to claim 2, of the general formula

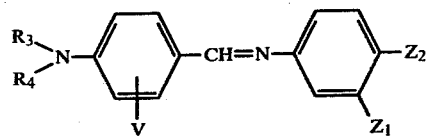  (3)

wherein
of Z₁ and Z₂ one represents a group of the formula (2a)

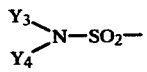  (2a)

and the
other represents hydrogen, halogen, lower alkyl or lower alkoxy and

V represents hydrogen, halogen, methyl, methoxy or ethoxy.

4. A process for the manufacture of azomethine compounds as defined in claim 1, which comprises reacting an aldehyde compound of the general formula

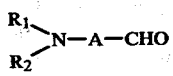  (6)

with an amino compound of the general formula $NH_2-B-X$  (7)

wherein A, B, R₁, R₂ and X have the meanings given in claim 1.

* * * * *